US006991649B2

(12) United States Patent
Sievers

(10) Patent No.: US 6,991,649 B2
(45) Date of Patent: Jan. 31, 2006

(54) ARTIFICIAL HEART VALVE

(76) Inventor: Hans-Hinrich Sievers, Laubenkoppel 22, 24119 Kronshagen (DE)

( * ) Notice: Subject to any disclaimer, the term of this patent is extended or adjusted under 35 U.S.C. 154(b) by 0 days.

(21) Appl. No.: 10/675,530

(22) Filed: Sep. 30, 2003

(65) Prior Publication Data
US 2005/0049697 A1 Mar. 3, 2005

(30) Foreign Application Priority Data
Aug. 29, 2003 (DE) ................................ 103 40 265

(51) Int. Cl.
*A61F 2/24* (2006.01)
(52) U.S. Cl. ..................................... 623/2.23; 623/2.26
(58) Field of Classification Search ....... 623/2.17–2.27
See application file for complete search history.

(56) References Cited
U.S. PATENT DOCUMENTS
4,306,319 A * 12/1981 Kaster ........................ 623/2.24
4,655,772 A * 4/1987 De Liotta et al. ........... 623/2.24
4,820,299 A * 4/1989 Philippe et al. ............. 623/2.23
5,843,183 A * 12/1998 Bokros et al. .............. 623/2.22
6,086,612 A * 7/2000 Jansen ........................ 623/2.17
6,113,631 A * 9/2000 Jansen ........................ 623/2.17
6,296,663 B1 * 10/2001 Patke et al. ................. 623/2.28
6,761,736 B1 * 7/2004 Woo et al. .................. 623/2.42
2001/0025197 A1 * 9/2001 Shu et al. ................... 623/2.31

* cited by examiner

Primary Examiner—Corrine McDermott
Assistant Examiner—Suzette J. Gherbi
(74) Attorney, Agent, or Firm—Klaus J. Bach

(57) ABSTRACT

In an artificial heart valve for the replacement of an aortic or a mitral valve, including an annular body, which is provided at its outer circumference with means for mounting the artificial valve in place by surgical procedures and which defines in its interior a blood flow passage in which valve flap elements are pivotally supported so as to open or close the blood flow passage depending on their pivot positions, the annular body includes circumferentially spaced projections extending into the flow passage and being provided at their inner ends with pivot joints on which the valve flap elements are pivotally supported.

16 Claims, 10 Drawing Sheets

Fig. 3 Section A – B
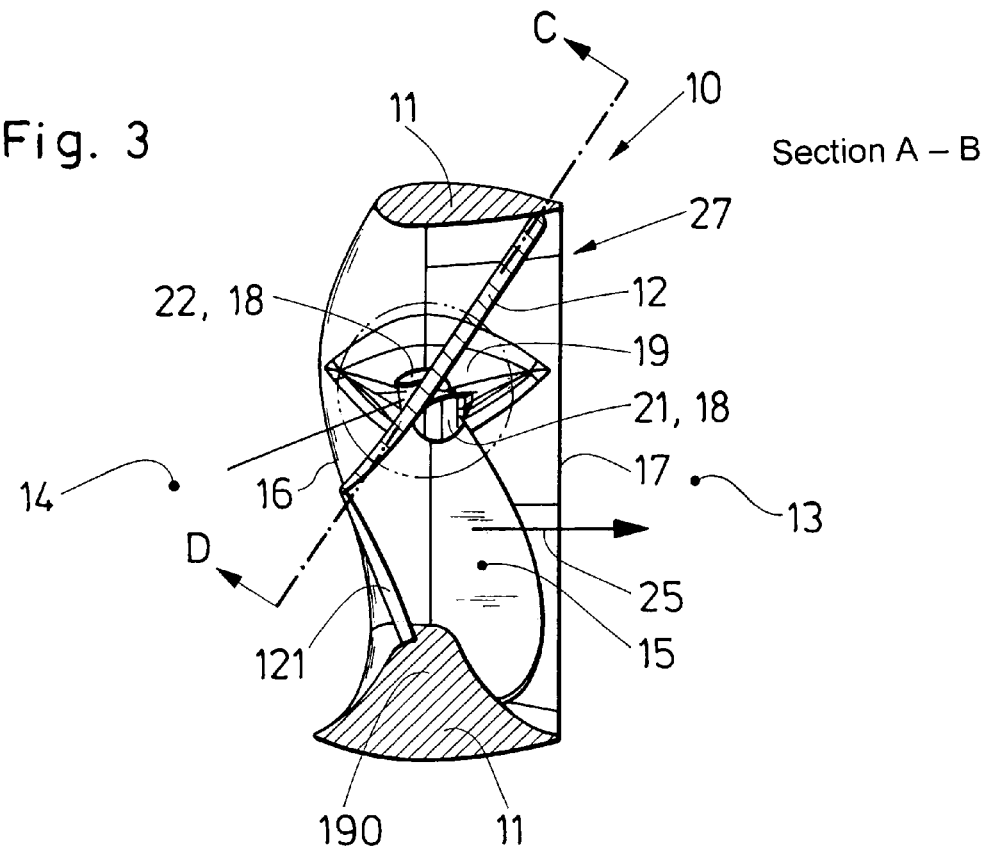
Fig. 4 Section C – D
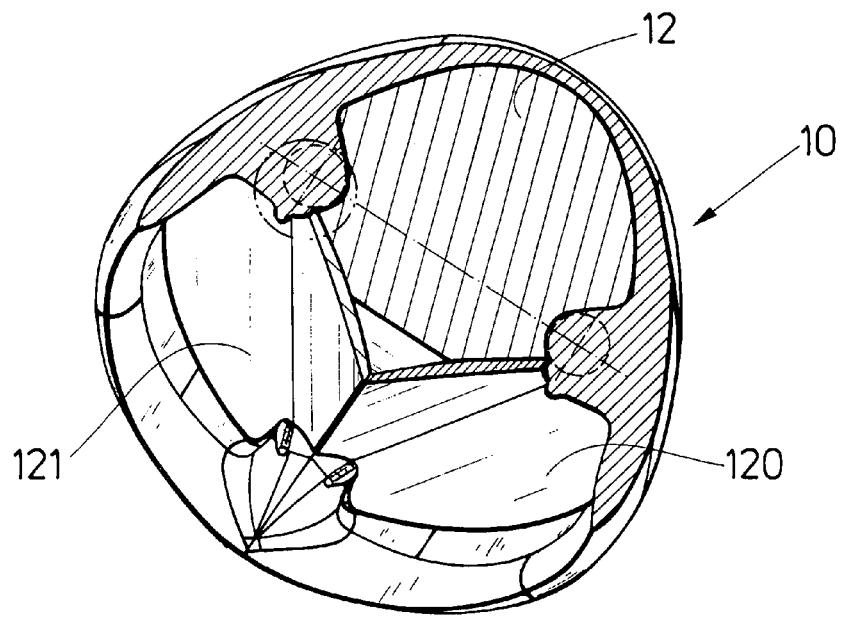

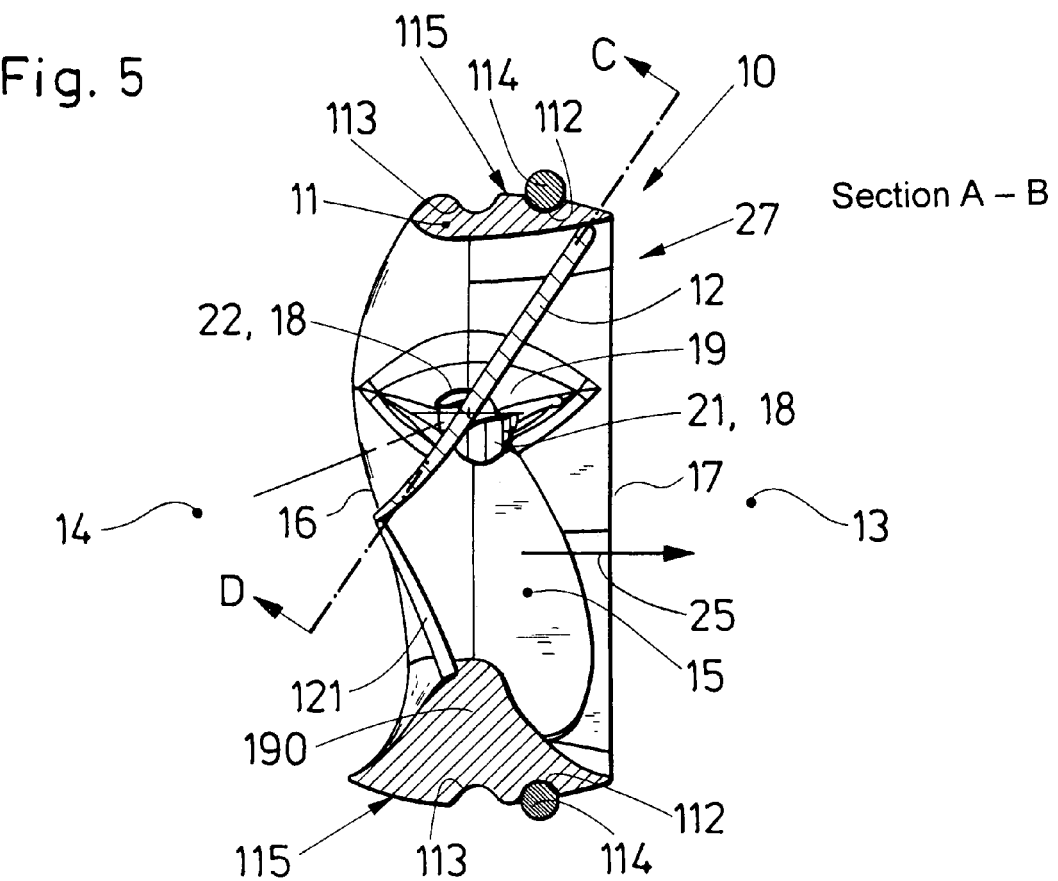
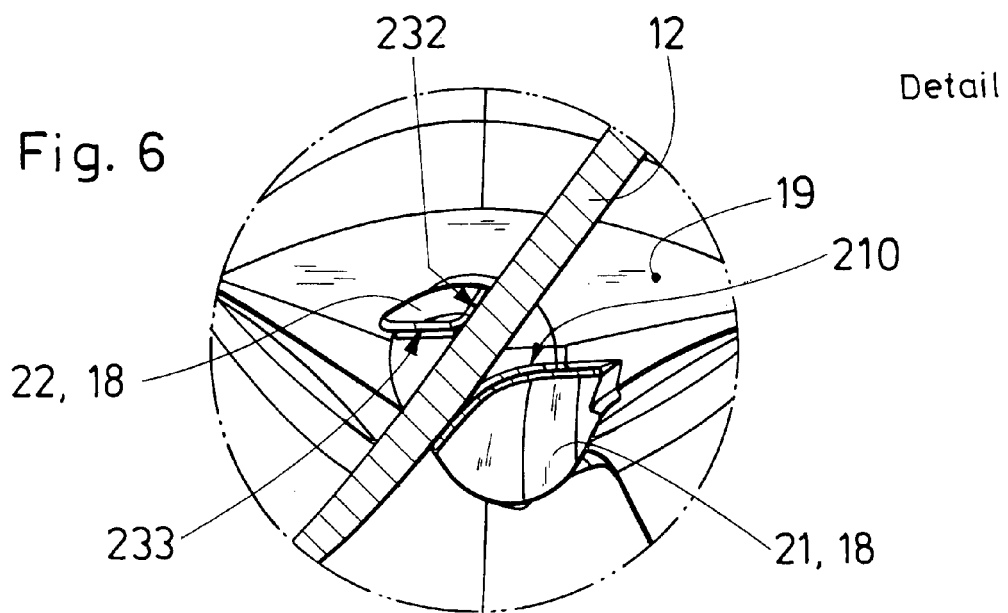

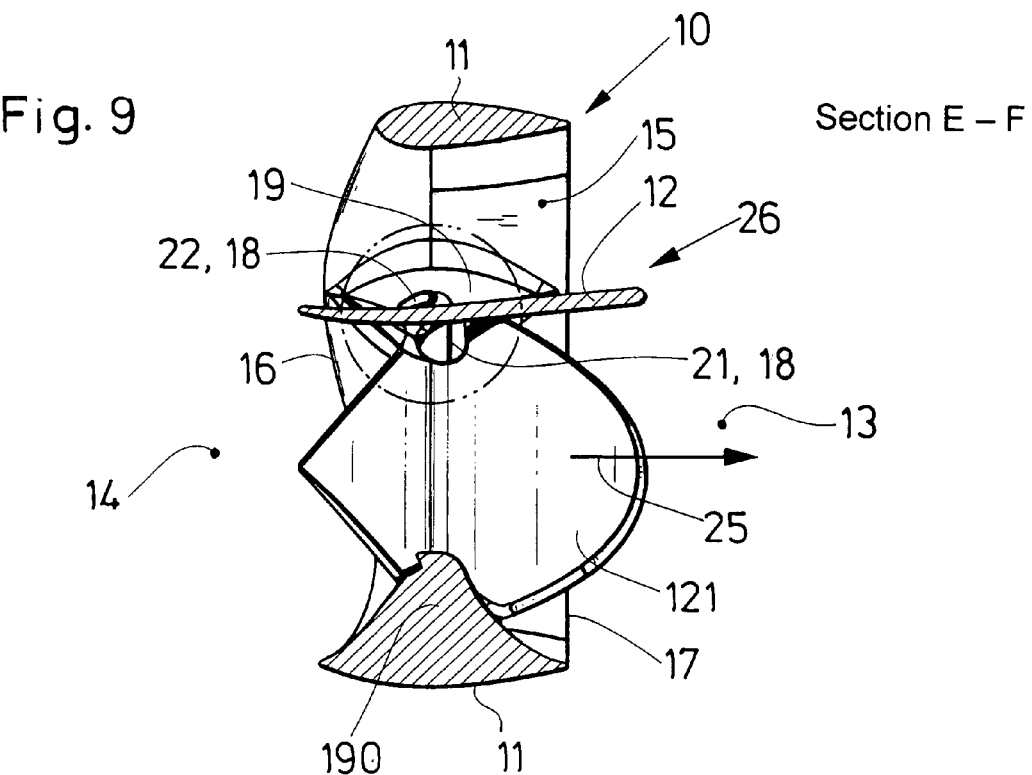
Fig. 9  Section E – F
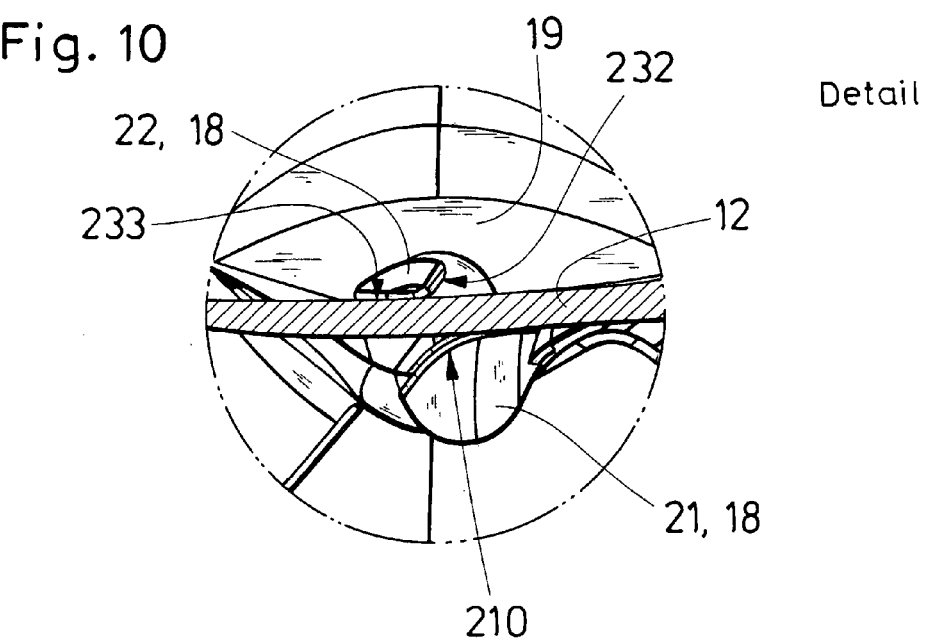
Fig. 10  Detail

Section G – H

ARTIFICIAL HEART VALVE

BACKGROUND OF THE INVENTION

The invention relates to artificial heart valves, that is, to a prosthesis for the replacement of aortic and mitral valves of a heart, comprising an annular body receiving a plurality of pivotal flap elements which annular body can be mounted into the aorta or the mitral valve ring and can be retained therein by surgical procedures so that the flap elements open or close the passage through the valve ring depending on their pivot positions.

A prosthesis, that is an artificial heart valve, of this type is known from WO-A-8504094. For some decades now, heart valve prostheses have been implanted into the aorta leading away from the heart. The first artificial heart valves were ball-type check valves which, with time, were replaced by more sophisticated designs. Heart valves with single flap elements and also with three-flap elements are known. The valve disclosed in WO-A-85 04094, for example, is a three-flap valve. Heart valves with flap elements use an annular support body on which the flap elements are pivotally supported and which is inserted for example into the aorta and is secured in position by a surgical procedure such as suturing.

The annular body is generally provided with shaft-like projections, which extend into corresponding openings of the flap element thereby forming a pivot joint. The flap element generally is provided with such openings at opposite sides with a shaft extending from the annular body into each of the opposite openings. However, also other solutions are known from the state of the art, wherein shaft-like projections extend from the flap elements into corresponding openings formed in the annular support body.

The opening and closing of the flap element, or of the flap elements, if more than one flap element are provided in the annular body, occurs in principle over long periods of use in a trouble-free manner since certain components of the blood act as lubricants which reduce friction in the joint parts.

However, all artificial heart valves of this type have the disadvantage that the joint area between the annular body and the flap elements negatively affect the flow dynamics of the blood through the opening of the annular body so that zones are formed in the joint areas in which blood is stagnant. This effect is generated also by the fact that the flap elements never move fully away from the annular body during the heart pumping cycle. In the areas in which the blood is stagnant in these valves blood clots are formed which are released from time to time and are then transported with the blood flowing through the aorta into remote body parts for example into the brain where they may block the blood passages with catastrophic results for the person affected thereby.

It has been tried with sophisticated designs to reduce to a minimum the areas near the joints where the blood can stagnate in order to minimize the chances of blood clot formation and it has also been tried to arrange the joints or the joint areas in such a way that the areas between the joint and the annular body are flushed by the blood flowing through the annular body so that these areas are kept "clean", in order to avoid the formation of blood clots but no really satisfactory solutions have been found. Consequently, heart valves with two flap elements (so-called double wing flaps) or ball-type heart valves which have no joints but which have substantial other disadvantages are still being used.

It is therefore the object of the present invention to provide a heart valve of the type described above which however does not have the disadvantages of the state of the art heart valves as pointed out above. The heart valve should, in its design, be adapted with regard to its physical-mechanical operation to the design of the natural heart valve and be capable of remaining in the body indefinitely after implantation while providing for trouble-free operation without the danger of forming blood clots. Also, the decreasing and increasing pressure of the blood as it occurs during opening and closing of the valve should correspond essentially to the pressure gradients occurring naturally in the heart during the opening and closing of the natural heart valves. It is further an essential object of the invention to provide an artificial heart valve of the type described above, which, after implantation, does not require the continuous administration of medication in order to prevent the formation of blood clots so that, in principle, the patient can live after heart valve implantation normally, that is, without having to take medications.

SUMMARY OF THE INVENTION

In an artificial heart valve for the replacement of an aortic or a mitral valve, including an annular body which is provided, at its outer circumference, with means for mounting the artificial valve in place by surgical procedures and which defines in its interior a blood flow passage in which valve flap elements are pivotally supported so as to open or close the blood flow passage depending on their pivot positions, the annular body includes circumferentially spaced projections extending into the flow passage and being provided at their inner ends with pivot joints by which the valve flap elements are pivotally supported.

The heart valve according to the invention employs principles for the design of the joints between the flap elements and the annular body, which are completely different from those used in the prior art designs. The joint at the annular body, which forms with the joint at the flap element a pivot joint, is intentionally so arranged that the pivot axis for the flap element is moved toward the center of the annular body that is toward the longitudinal center axis of the aorta in order to move the joint as far as possible into the area of the highest flow speed of the blood. As a result, all areas of the respective joint between the flap elements and the annular body are in contact with the fast flowing blood through the center area of the annular body so that no areas of stagnant blood can develop in the joint areas and the formation of blood clots is essentially prevented.

Another important advantage of the arrangement according to the invention is that in this way closing is initiated timely during the forward flow of the blood (systolic). In the artificial heart valves presently in use the valve closing occurs mainly passively during the relaxation phase of the heart by a return blood flow.

In an advantageous embodiment of the artificial heart valve, the pivot joints are formed on projections, which extend inwardly from the annular body and have at their inward ends remote from the annular body a pair of spaced webs which are oriented in the flow direction of the blood through the annular body and which form together a body-based joint structure. The joint structure at the annular body is therefore exposed to the fast blood flow in the center area of the annular body. Also, the space between the two webs is exposed to the fast blood flow, since the two webs extend into the blood flow path in spaced relationship from each other so that the blood can flow along both sides of each web. At the end of the joint next to the annular body, there are therefore no areas, in which blood can become stagnant so that also no blood clots can form.

In another advantageous embodiment, at least one of the webs may be formed integrally with the support web for an adjacent flap element so that fewer edges or recesses are present on which blood can be deposited and the blood flow flushes the joint area even more thoroughly.

In still another advantageous embodiment of the artificial heart valve, the joints of the flap elements are formed at the flaps by two shallow recesses disposed essentially symmetrically with respect to a centerline of the essentially flat flap elements, that is, the joint structure at the flap element has no projections or bores or similar areas which are not exposed to the stream of blood.

The joint part of the annular housing and the joint part of the flap element form therefore a joint in that the flap element is pivotally engaged in the area of the recess between the spaced webs of the respective projections of the annular body. Between the two webs of the annular housing joint part and the joint part of the flap element engaged between the two webs, there is sufficient play that the blood flowing through the annular housing opening can also flow through all areas of the joint, that is, that there are no areas in which any blood stagnates. The part of the projection into which the flap element extends between the webs is preferably spherically shaped so that no, or only little, resistance is provided in the joint area to the passage of blood.

In order to prevent the flap elements from abruptly reaching the closed position which could result in cavitation effects because of the high pressure gradients occuring thereby and which therefore could cause damage to, or even destroy, the blood, the web of the pair of webs which is disposed at the upstream side of the heart valve may be provided with a joint surface which extends essentially orthogonally to the flow direction of the blood through the annular body and on which the flap element rolls during its opening and closing movements. With this measure, the flap elements are closed in a controlled manner while the blood is still flowing into the aorta and the force with which the flap elements engages the annular housing upon closing of the valve is reduced. Since, with this measure, extreme pressure gradients in the blood can be avoided, the blood is also not subjected during the closing of the flap elements to cavitation effects which might destroy the blood.

In a further advantageous embodiment of the artificial heart valve, the web at the downstream side that is remote from the heart is provided with two stop surfaces, which extend essentially orthogonally to the flow direction of the blood through the annular body and which define the open and the closed positions of the flap element. In this way, no other stops or limits are required which may have to extend into the flow passage of the blood and which form areas in which the blood may stagnate.

Preferably, the flap elements of the artificial heart valve are spherically shaped wherein the sphere may be formed with any degree of freedom. Such a "belly-like" shape of the flap elements prevents a so-called flow equilibrium, that is, the flap elements may open completely during the opening phase until they reach the stop and provide for an effective flow of blood over the surfaces and through the joints which additionally prevents the deposition of particles and the formation of clots of blood. The spherical shape of the flap elements results also in an early initiation of the closing of the flap element because, the blood flow becomes smaller already in the systolic phase (forward flow) of the heart pumping cycle. Therefore, for the final closing step only a small back flow volume is required, with the advantageous result that also the strain on the heart is reduced.

Preferably, the inner part of the flap element, which spans the area between the pivot axis of the valve flap and the center tip of the valve flap which extends in the case of the aorta toward the heart when the valve is open, is angled with respect to the outer part of the valve flap so that, with the valve fully open, the inner part of the valve flap extends parallel to the flow direction of the blood and prevents therefore the generation of turbulence. The angled part of the valve flap may also be spherical in shape.

As a result of the arrangement of the joints at the free ends of the projections extending inwardly from the annular body and the flaps supported in recesses formed about in the middle along their sides and because of the spherical shape of the flap elements, the flap elements move fully away from the annular body during opening so that all areas of the artificial valve are exposed to the flowing blood when the valve is open.

The artificial heart valve according to the invention is basically operable with only one or two flap elements arranged in the annular body. It is however very advantageous to provide three flap elements which are arranged in the annular body with their pivot axes forming an equal-sided triangle extending between the support webs. In this way, a very advantageous "three-wing-valve" is provided by the arrangement according to the invention whereby an artificial valve is formed which is very close in design to the natural heart valve.

On the basis of this arrangement, the artificial valve may be refined by selection of suitable arrangements and sizes of the flap elements in the annular body such that four flow passages are formed in the annular body which have about the same flow cross-section. With a "three-wing-valve" four passages with equal flow cross-sections can be provided, i.e. a central flow passage and three flow passages delimited by the annular support body for permitting a large essentially uninhibited blood flow through the open valve.

It is also advantageous if the inner flow cross-section of the annular body from the blood inlet adjacent the heart toward the outlet at the end remote from the heart becomes first smaller up to the plane in which the projections are disposed and then becomes again larger by the outwardly curved surfaces of the flaps to provide a venturi nozzle flow profile similar to the flow profile of the natural heart valve.

During implantation of the artificial heart valve, the diameter of the aorta is relatively small because there is no internal pressure. For this reason, the outer circumference of the annular body has a conical shape that is it increases toward the axial center of the annular body so that the annular body can be inserted easily into the aorta while dilating the aorta to its normal diameter which it has when exposed to the pressure of the blood.

In order to fix the artificial heart valve at the implantation location in a sealed fashion, the annular body has formed in its outer wall two spaced annular grooves of which the first groove, which is closer to the heart accommodates the remaining tissue of the natural heart valve.

Preferably, a suturing ring is received in the second groove, which is more remote from the heart than the first groove by way of which the tissue is sutured to the artificial heart valve during implantation.

As materials for the annular body and/or the flap elements basically any material is suitable which has a high durability and a low weight and which furthermore is compatible with the biological tissue.

Metal alloys or elemental metals may be used for the annular body and/or the flap elements. But also plastic materials and plastic compound materials may be used for the annular body and/or the flap elements.

It is particularly advantageous if the annular body and/or the flap elements are made from titanium or a titanium alloy since titanium and titanium alloys are high-strength metals with a relatively low weight and low wear which is particularly advantageous for the joint areas of the artificial heart valve. Particularly suitable are titanium-tantalum alloys.

In order to increase the resistance to wear of the materials, from which the annular body and/or the flap elements are formed, and to increase their biocompatibility, it is advantageous to coat the annular body and/or the flap elements with a hard material layer for example of boron-carbide or a similar layer which may be applied by well-known classic coating processes such as the PVD process (physical vapor deposition) and/or the CVP process (chemical vapor deposition).

The invention will be described below in greater detail on the basis of the accompanying drawings:

BRIEF DESCRIPTION OF THE DRAWINGS

FIG. 3 is a cross-sectional view taken along line A–B of FIG. 1, FIG. 4 is a sectional view taken along line C–D of FIG. 3, FIG. 5 is a sectional view taken along line A–B of FIG. 1, wherein, in this representation, two grooves extend around the annular body and a suturing ring for anchoring the artificial heart valve in the tissue is shown in one of the grooves, FIG. 6 is an enlarged representation of the detail encircled in FIG. 3, FIG. 9 is a sectional view taken along line E–F of FIG. 7, FIG. 10 is an enlarged view of the detail encircled in FIG. 9.

DESCRIPTION OF PREFERRED EMBODIMENTS

Figure 1:
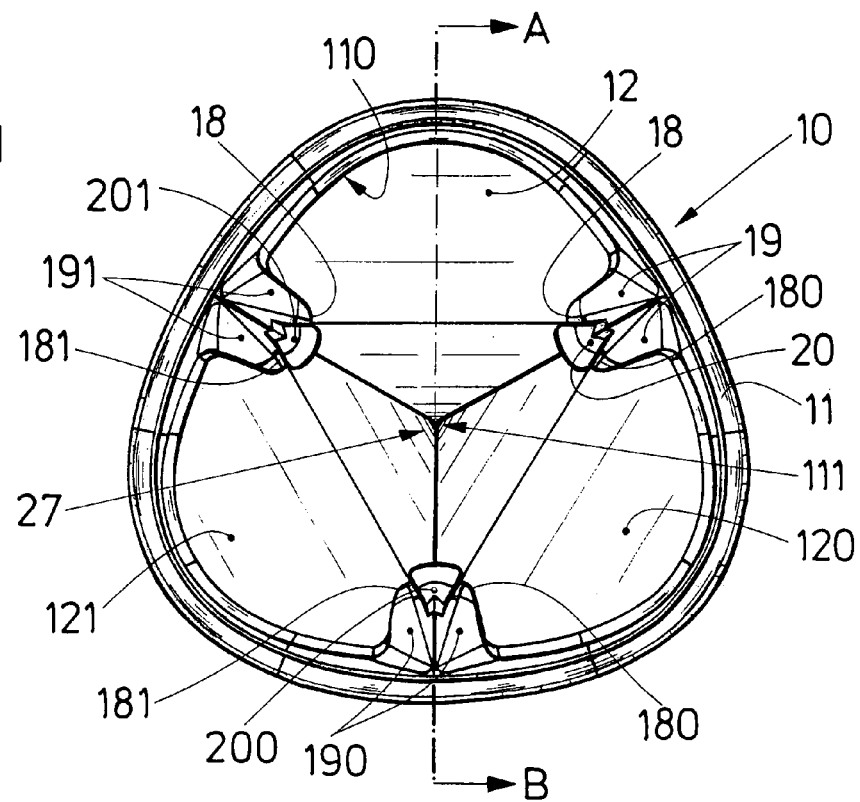
FIG. 1 is an enlarged representation of an artificial heart valve according to the invention shown in a top view and in a closed position.
Figure 2:
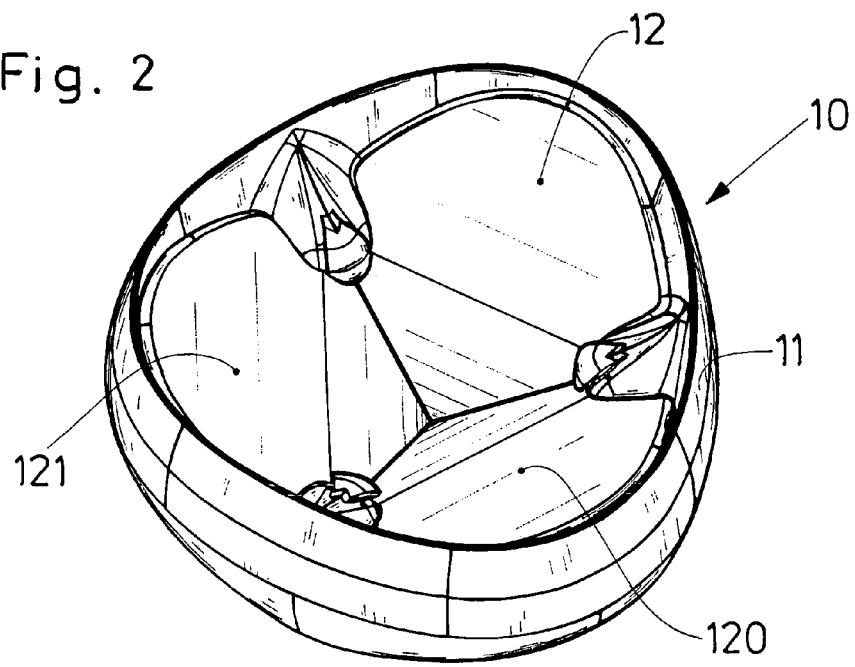
FIG. 2 is a perspective view of the artificial heart valve shown in FIG. 1.
Figure 7:
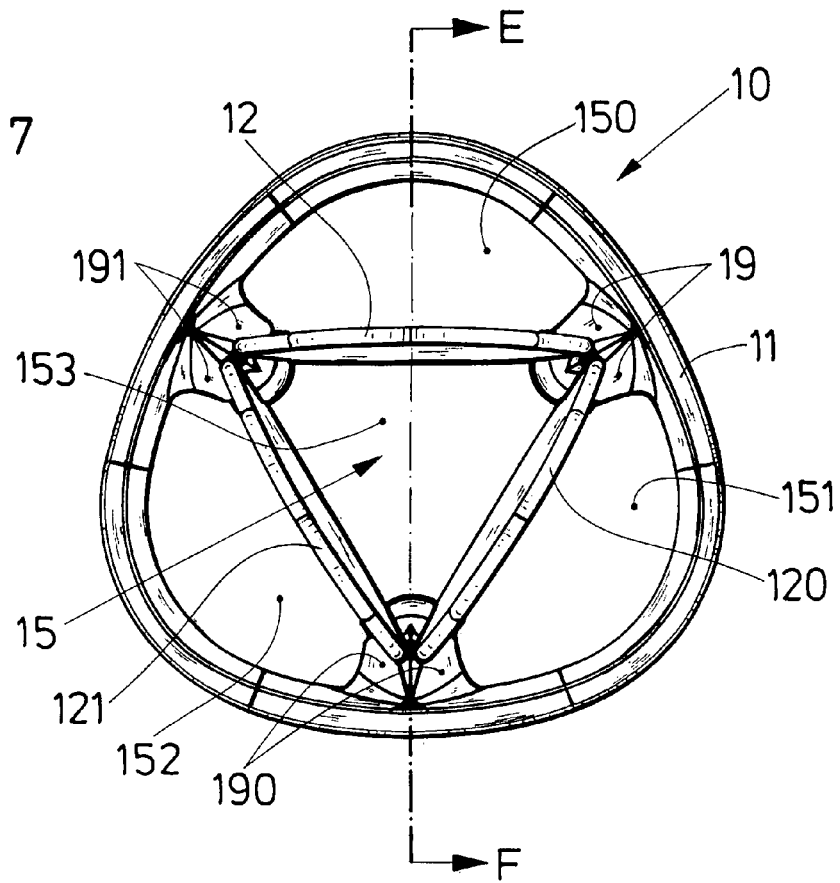
FIG. 7 shows the artificial valve in a top view with the flap elements in open positions.

First reference is made to FIG. 1 where the artificial heart valve 10 is shown in a closed position and to FIG. 7 where the artificial heart valve 10 is shown in an open position. The FIGS. 1 and 7 are top views showing the heart valve 10 from that side, which, after implantation of the heart 14, faces the heart 14.

The artificial heart valve 10 comprises essentially an annular body 11, which has a shape resembling an equal-sided triangle with rounded corners. The annular body 11 however may also be circular or have a cross-section of another form. The artificial heart valve 10, described below as an example, includes three flap elements 12, 120, 121, however, in principle, the inventive concept can be realized also with a valve having only one flap element or two flap elements. Also designs with more than three flap elements 12, 120, 121 are conceivable. The annular body 11, which is insertable into the aorta 13 and the heart 14 in a known manner and which can be fixed there in place supports the three flap elements 12, 120 and 121 in a pivotable manner such that, depending on the pivot position of the flap elements 12, 120 121 the passage for the blood pumped by the heart 14 to the aorta 13 is open and the blood can flow through the inner passage 15 of the annular body 11, see FIG. 7 or the passages is closed as shown in FIG. 1. The mechanism as such is well known in principle in connection with all artificial valves of this type so that the operation of a heart valve does not need to be described.

The annular body 11 includes three essentially identical projections 19, 190, 191 arranged equally spaced on the annular body 11 and formed integrally with the annular body so as to extend inwardly. The projections 19, 190, 191 are shaped in the longitudinal and transverse cross-section in such a way, that an essentially laminar flow of the blood through the inner opening 15 of the annular body 11 is ensured. To this end, the projections are provided with transverse and longitudinal profiles which generate the lowest possible hydrodynamic resistance for the blood flowing through annular body 11, see also the cross-sectional view of FIG. 3 taken along line A–B of FIG. 1, and the detail of FIG. 3 shown in FIG. 6.

The projections 19, 190, 191 extend into the interior 15 of the annular housing for a length of about 45% of the distance between the inner housing wall 110 and the axial center line 111. It is noted however, that the projections 19, 190, 191 may have different lengths, which may be selected in adaptation to the conditions of a patients heart, into which the valve is to be implanted. The length of 45% of the distance between the inner annular housing wall and the center thereof is exemplary to show that the projections may be relatively long so that the ends 20, 200, 201 are disposed in the area of the largest blood flow through the flow passage 15 of the annular body 11. The flap elements 12, 120 121 are supported at the ends 20, 200, 201 of the projections 19, 190, 191 by pivot joints 18, 180, 181. In the embodiment as shown in the figures, the respective joints 18, 180, 181 are double joints so that each projection 19, 190, 191 carries actually two joints 18, 180, 181, see particularly FIGS. 1 and 7, each projection supporting one end of adjacent flap elements 12, 120, 121. As a result, only three projections with joints are needed to project into the flow passage 15 of the artificial valve, which provides for minimal disturbance of the laminar flow through the valve, whereas in prior art valves six joint support structures were needed with all the disadvantages of such a design, particularly the higher hydrodynamic resistance. At each projection 19, 190, 191, the pivot joints 18, 180, 181 are formed by two spaced webs 21, 22, which are oriented toward the longitudinal axes 111 and in the flow direction 25 of the blood through the valves, see FIGS. 3, 6, 9 and 10. The two webs 21, 22 form jointly a pivot joint part 18, 180, 181. In the artificial valve 10 described herein which has three flap elements 12, 120, 121, six such pivot joints (joint pairs 18, 180, 181) consisting of web pairs 21, 22 are formed.

The web 21 remote from the heart extends essentially normal to the flow direction 25 of the blood through the annular body 11. It is provided with a curved joint surface 210. The curved joint surface 210 supports the valve flap in such a way that, during the opening and closing pivot movement, it can roll on the curved surface 210, see FIG. 3, the detail of FIG. 6, FIG. 9 and the detail of FIG. 10. The web 22 of the pair of webs at the side next to the heart, that is at the pressure side, extends also essentially normal to the flow direction 25 of the blood through the annular body 11. Instead of the curved pivot surface 210 of the web 21, the web 22 is provided with two stop surface areas 232, 233. The stop surface areas 232, 233 delimit the open end position 26, see FIG. 9 and the detail of FIG. 10, and the closed position 27 of the flap elements 12, 120, 121, see FIG. 3 and the detail FIG. 6.

Figure 12:
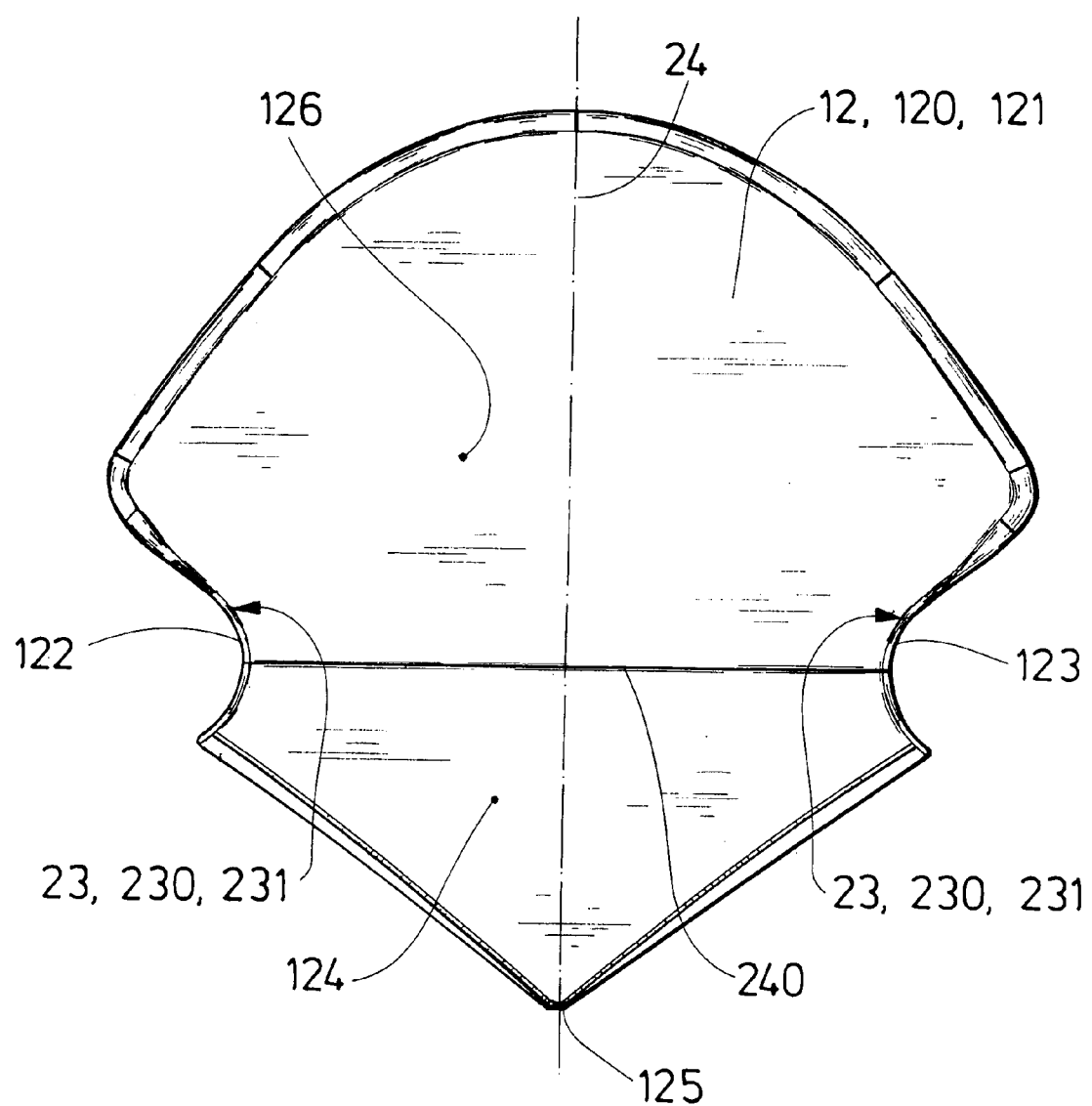
FIG. 12 is an enlarged representation of a valve flap.
Figure 13:
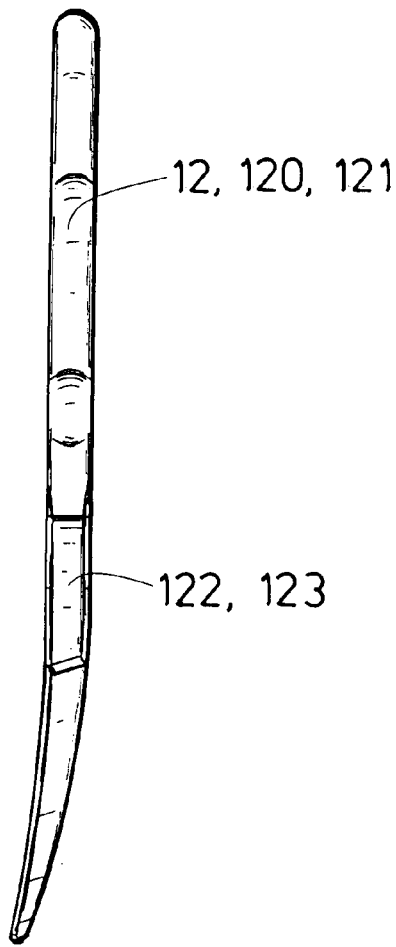
FIG. 13 is a side view of the flap element as shown in FIG. 12.
Figure 14:
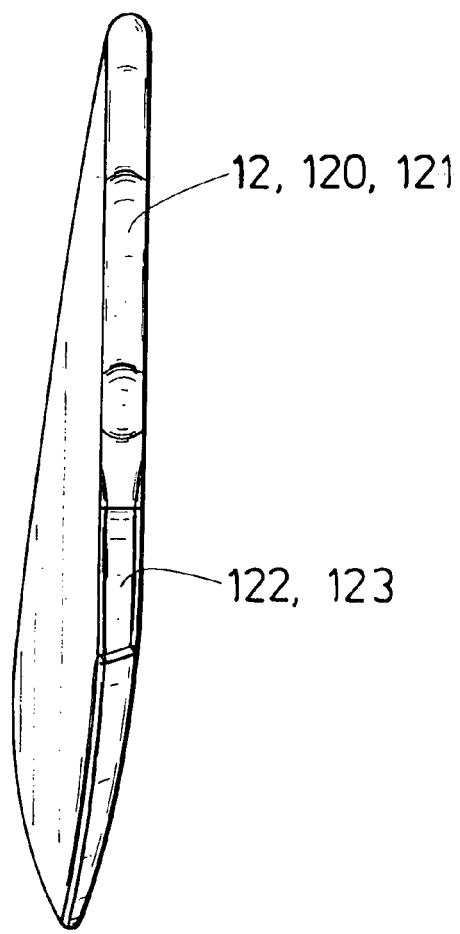
FIG. 14 is a side view of a flap element as shown in FIG. 12, wherein however the flap has a spherically curved top surface.
Figure 15:
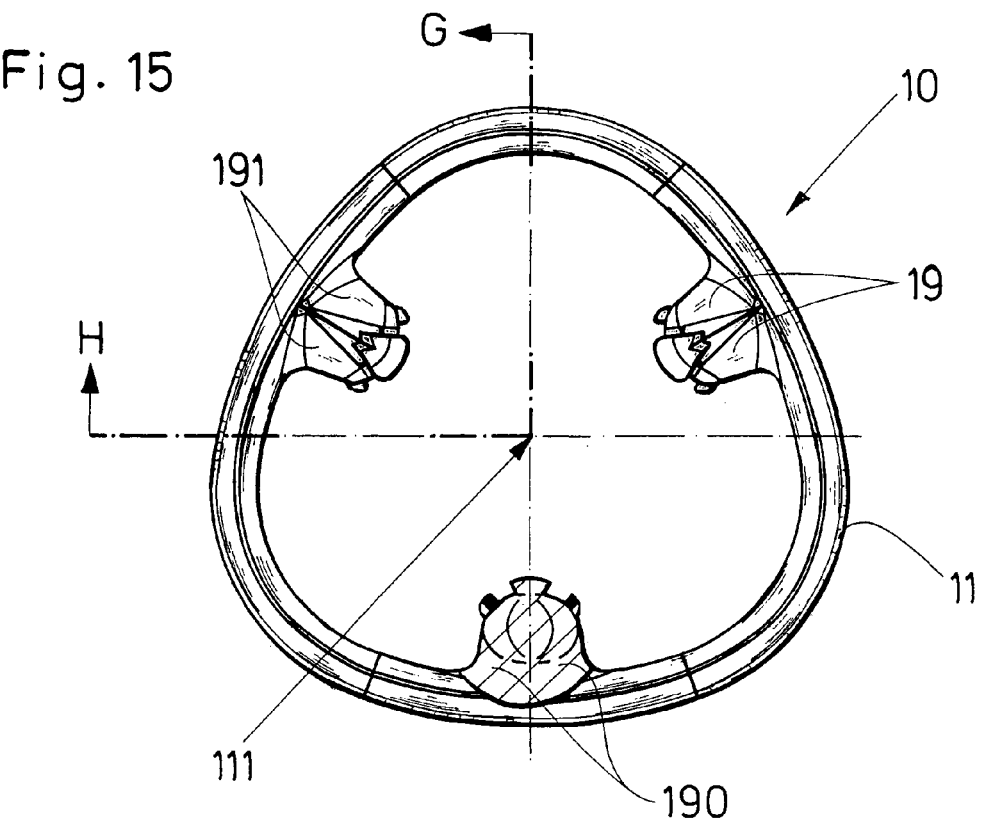
FIG. 15 shows an annular body of the artificial heart valve according to the invention with the flap elements removed to show more clearly the projections extending into the interior of the annular valve body, one of the projection carrying the joint being shown in cross-section.
Figure 16:
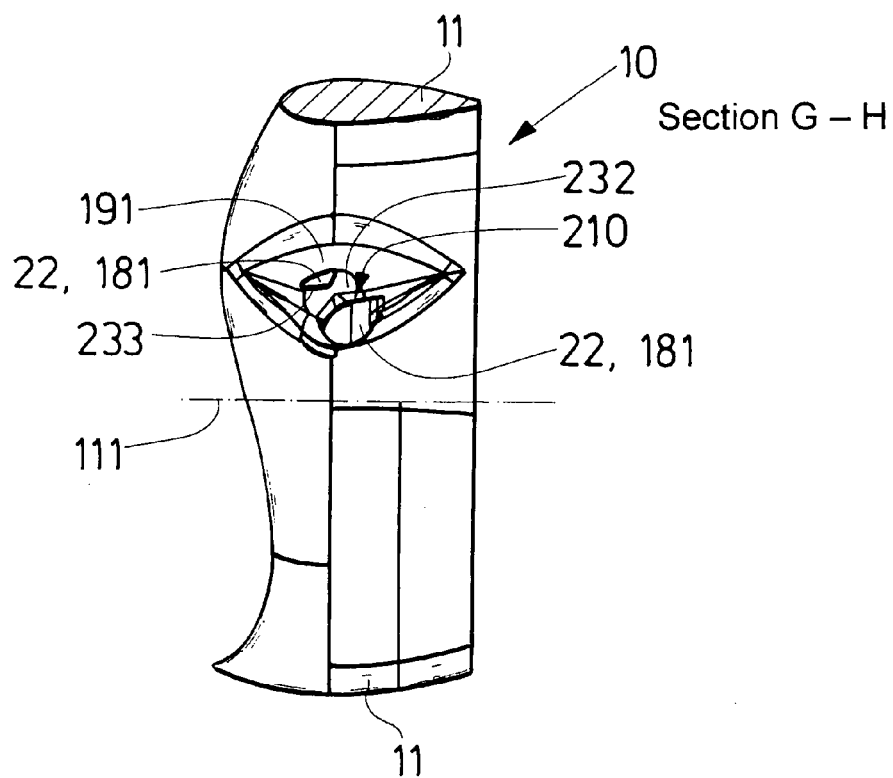
FIG. 16 is a sectional view taken along line G–H of FIG. 15.
Figure 17:
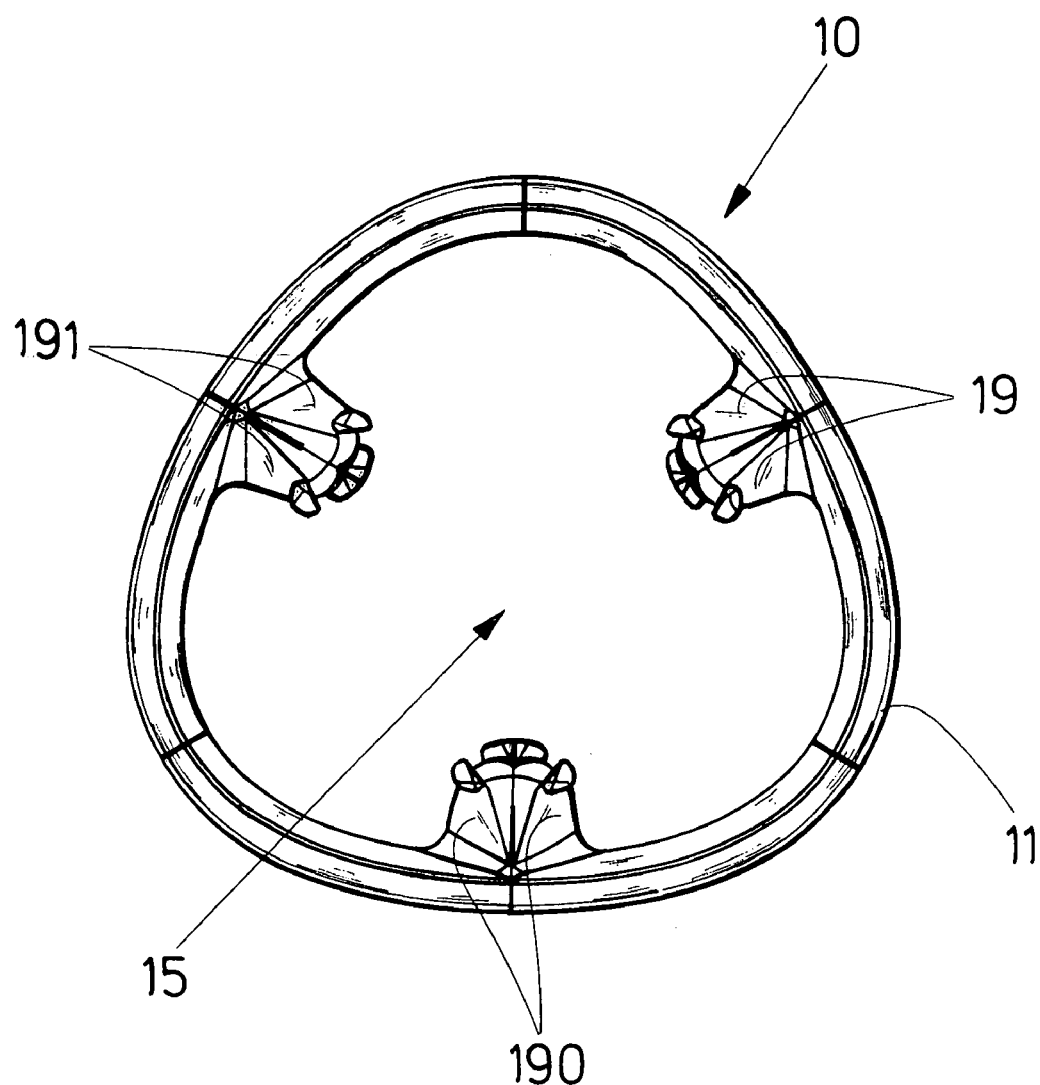
FIG. 17 shows the annular body in a top view from the rear without flap elements.

The joint areas 23, 230, 231 at the flap elements 12 that is the joint 23, 230, 231 of each flap element 12, 120, 121 are provided by recesses 122, 123 arranged at opposite sides of the flap 12, 120, 121 at the pivot center line 240, see FIG. 12. The flap elements 12, 120, 121 are curved at least in one cross-sectional plane, see FIG. 13, but the flap elements 12, 120, 121 may also be curved spherically as indicated in FIG. 14. The joints, or respectively, the joint parts 23, 230, 231 of the flap elements 12, 120, 121 are represented merely by recesses 122, 123 in the surfaces of the flap elements 12, 120, 121. With this simple, but highly effective and functionally optimized form, wherein no bores or shaft bolts or similar devices are provided, the full joint between the joint parts of the annular body, that is, the joint parts 18, 180, 181 and the flap-side joint parts 23, 230, 231 are formed in that the flap element 12, 120, 121 is engaged from opposite sides in the area of the recesses between the spaced webs 21, 22.

The flap element 12, 120, 121 is therefore pivotally supported on the annular body by ways of the webs 21, 22 formed on the respective projections 19, 190, 191.

Figure 8:
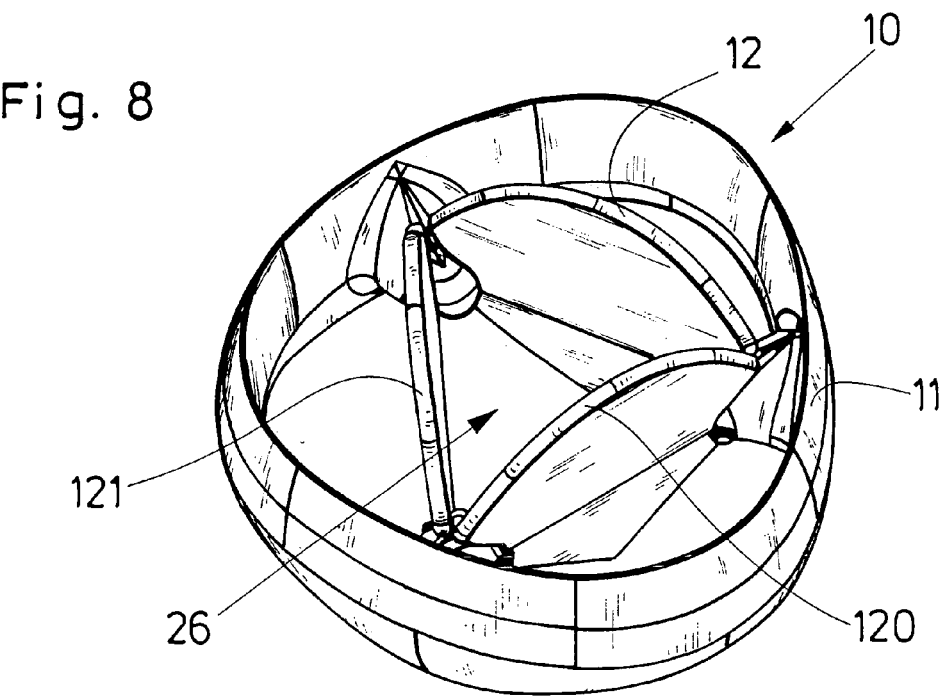
FIG. 8 is a perspective view of the valve as shown in FIG. 7.
Figure 11:
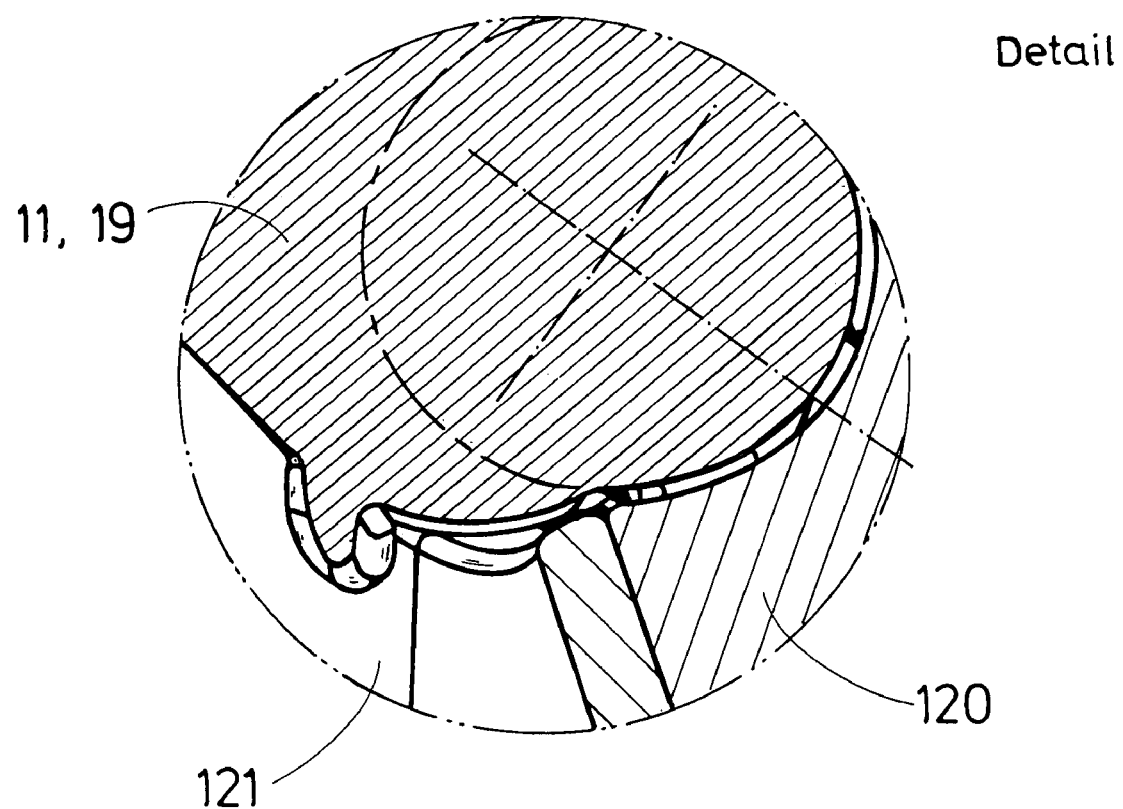
FIG. 11 is an enlarged view of the detail encircled in FIG. 4.

As shown particularly in FIGS. 7 and 8, in the open position of the flap elements 12, 120, 121, four flow passages 150, 151, 152, 153 of essentially equal flow cross-sections are formed in the flow passage 15 through the annular body 11. By suitably arranging and dimensioning the flap elements 12, 120, 121 in the annular body 11, the flow passages 150, 151, 152 and 153, which consequently provide essentially for the same flow restriction in all the flow passages and therefore for essentially the same flow volumes and flow speeds in the different passages so that turbulence effects at the downstream end of the individual passages is avoided.

As shown particularly in FIGS. 3 and 9, which show a cross-section through the annular body 11, the flow passage 15 is so shaped that, in the flow direction of the blood, it becomes first smaller up to the plane in which the projections 19, 190, 191 extend, but then becomes wider again toward the outlet opening 17 into the aorta. The narrowing flow inlet section is substantially shorter than the widening outlet section of the flow cross-section 15 so as to provide a low-restriction venturi-type passage. Also the outer diameter of the annular body 11 increases from the inlet opening 16 essentially up to the plan in which the projections 19, 190, 191 are disposed so that stretching of the aorta 13 during implantation of the artificial valve is facilitated since, during implantation, the aorta 13 is not subjected to internal blood pressure and is therefore smaller than when subjected to pressure. With the design of the annular body 11 as described above the artificial valve may be relatively large so that the pressure gradient in the blood flow through the valve is relatively small and there is little pressure loss generated by the valve and flow turbulence is minimal.

At its outer surface 115, the annular body has grooves 113, 112 of a semicircular cross-section extending circumferentially around the annular housing 11 in an axially spaced relationship. In the groove 113, closer to the heart 14, the remaining tissue is accommodated. In the groove 112, remote from the heart a suturing ring 114 is disposed which also surrounds the annular body 11. The suturing ring 114 is firmly and sealingly received in the groove 113. The suturing ring 114 may consist of a suitable plastic material so that the aorta tissue can be attached by a suitable suturing procedure.

As mentioned already earlier, the annular body may be formed integrally as an injection molding component or it may be manufactured by powder metallurgical methods, which is also true for the flap elements. The annular body 11 and/or the flap elements 12, 120, 121 may also be coated with a hard material layer in order to avoid a necrologic effect of some of the metal alloys which may be used for the manufacture of an artificial heart valve 10 and to ensure biocompatibility with the biological tissue. They also may be provided with a hard and wear resistant layer, particularly in the area of the joints 23, 18, 230, 180 and 231, 181 between the annular body 11 and the flap elements 12, 120, 121. With the application of such a layer no wear occurs between, or in, the joints of the artificial valve 10.

Basically, the annular body may also be assembled of different, that is separate, parts; it may consist for example of three parts which are joined suitably after the mounting of the flap elements 12, 120, 121 in the joints 18, 23, 180, 230, 181, 231.

With a one-piece configuration of the annular body 11 the flap elements 12, 120, 121 could be somewhat elastic so that they could be snapped into position between the respective webs 21, 22 of the projections 19, 190, 191 by way of the recesses 122, 123.

The artificial heart valve 10 according to the invention has been described essentially in connection with an implantation thereof into an aorta 13. However, the heart valve 10 according to the invention may be used essentially with the same design as described also as a mitral valve.

What is claimed is:

1. An artificial valve for the replacement of an aortic or mitral heart valve, comprising: an annular body for installation into a valve flap ring of an aortic or mitral heart valve, said annular body including, at its outer circumference, means for mounting by surgical procedures and defining in its interior a blood flow passage, flap elements which are pivotally supported in said blood flow passage by pivot support structures and which, depending on their pivot positions, open or close said blood flow passage, said annular body including circumferentially spaced projections extending inwardly into said flow passage toward the center area of said blood flow passage, said spaced projections being provided at their inwardly extending ends with pivot joints on which said flap elements are pivotally supported, about a pivot axis extending through the pivot joints such that the cross-section covered by the outer part of each valve flap between the pivot axis and the annular body is larger than the flow cross-section covered by the flap in the center area of the annular body, whereby the outer valve parts adjacent the annular body are opened by the flow of blood through the valve in the direction of the blood flow and the inner valve flap parts projecting from the pivot axis into the center of the annular body are opened against the flow of the blood through the valve.

2. An artificial valve according to claim 1, wherein said flap elements have partial circular recesses formed therein symmetrically at opposite sides along a pivot axis of said flap elements and said projections have spherical ends received in said recesses and pivotally engaging said flap elements.

3. An artificial valve according to claim 2, wherein, in the area of said recesses, said flap element is engaged between two spaced webs arranged and formed so as to permit pivoting of said flap element between said spaced webs.

4. An artificial valve according to claim 3, wherein the, with respect to the blood flow through the valve, downstream web of the webs engaging a valve flap extends essentially normal to the direction of the blood flow through the annular body and has a curved joint surface on which said flap element rolls during the opening and closing movement thereof.

5. An artificial valve according to claim 4, wherein the upstream web of the webs engaging a valve flap extends essentially normal to the flow direction of the blood through the annular body and is provided with two stops defining the open and respectively, the closed position of the valve flap.

6. An artificial valve according to claim 1, wherein said flap elements are spherically curved.

7. An artificial valve according to claim 1, wherein said flap element has a pointed portion extending, in the closed position of the flap element inwardly from said pivot axis of said valve flap and a rounded portion disposed at the opposite side of pivot axis, said pointed and said rounded portions being angled with respect to each other.

8. An artificial valve according to claim 1, wherein said annular body and said flap elements consist of one of titanium and a titanium alloy.

9. An artificial valve according to claim 1, wherein at least one of said annular body and said flap elements is coated by a hard material layer.

10. An artificial valve for the replacement of an aortic or mitral heart valve, comprising: an annular body for installation into a valve flap ring of an aortic or mitral heart valve, said annular body including, at its outer circumference, means for mounting by surgical procedures and defining in its interior a blood flow passage, flap elements which are pivotally supported in said blood flow passage by pivot support structures and which, depending on their pivot positions, open or close said blood flow passage, said annular body including circumferentially spaced projections extending inwardly into said flow passage toward the center area of said blood flow passage, said spaced projections being provided at their inwardly extending ends with pivot joints on which said flap elements are pivotally supported, said projections being provided at their inwardly projecting ends with spaced webs extending further inwardly from said circumferentially spaced projections and being oriented in the flow direction of the blood through said passage and engaging said flaps so as to form said pivot support structure.

11. An artificial valve according to claim 10, wherein at least one of said webs on each of said projection is formed integrally with said projection.

12. An artificial valve for the replacement of an aortic or mitral heart valve, comprising: an annular body for installation into a valve flap ring of an aortic or mitral heart valve, said annular body including, at its outer circumference, means for mounting by surgical procedures and defining in its interior a blood flow passage, flap elements which are pivotally supported in said blood flow passage by pivot support structures and which, depending on their pivot positions, open or close said blood flow passage, said annular body including circumferentially spaced projections extending inwardly into said flow passage toward the center area of said blood flow passage, said spaced projections being provided at their inwardly extending ends with pivot joints on which said flap elements are pivotally supported, said valve including three flap elements so that, in the open position of said valve, four flow passages are provided, one central and three circumferential passages, between the projections and the respective valve elements, the location of the valve pivot axis and the form of the valve ring being so selected that all four blood flow passages have about the same flow cross-section.

13. An artificial valve for the replacement of an aortic or mitral heart valve, comprising: an annular body for installation into a valve flap ring of an aortic or mitral heart valve, said annular body including, at its outer circumference, means for mounting by surgical procedures and defining in its interior a blood flow passage, flap elements which are pivotally supported in said blood flow passage by pivot support structures and which, depending on their pivot positions, open or close said blood flow passage, said annular body including circumferentially spaced projections extending inwardly into said flow passage toward the center area of said blood flow passage, said spaced projections being provided at their inwardly extending ends with pivot joints on which said flap elements are pivotally supported, the interior flow passage through said annular body having a cross-section which decreases from the upstream end thereof toward said projections and then again increases from the area of said projections toward the downstream end of said passage.

14. An artificial valve according to claim 13, wherein the outside cross-section of said annular body increases toward the cross-sectional plane in which the projections are disposed.

15. An artificial valve according to claim 13, wherein said annular body is provided with two spaced annular grooves.

16. An artificial valve according to claim 15, wherein a suturing ring is firmly engaged in one of said circumferential grooves.

\* \* \* \* \*